United States Patent [19]

Shiga

[11] 4,354,505
[45] Oct. 19, 1982

[54] METHOD OF AND APPARATUS FOR TESTING AND INDICATING RELAXATION STATE OF A HUMAN SUBJECT

[75] Inventor: Kazumasa Shiga, Kawasaki, Japan

[73] Assignee: Matsushita Electric Industrial Company, Limited, Osaka, Japan

[21] Appl. No.: 183,750

[22] Filed: Sep. 3, 1980

[30] Foreign Application Priority Data

Sep. 4, 1979 [JP] Japan .................... 54-113744

[51] Int. Cl.³ .......................................... A61B 5/04
[52] U.S. Cl. .................................. 128/732; 128/905
[58] Field of Search ............... 128/731, 732, 733, 905

[56] References Cited

U.S. PATENT DOCUMENTS

| | | | |
|---|---|---|---|
| 3,837,331 | 9/1974 | Ross | 128/905 X |
| 3,967,616 | 7/1976 | Ross | 128/905 X |
| 3,978,847 | 9/1976 | Fehmi et al. | 128/732 |
| 4,031,883 | 6/1977 | Fehmi et al. | 128/732 |

OTHER PUBLICATIONS

Winson, J., "A Simple Sleep Stage Detector for the Rat", Electroencephalograph and Clin. Neureophys., vol. 41, No. 2, pp. 179–182, Aug. 1976.
Sciarretta et al., Med. & Biol. Engng., vol. 8, No. 5, pp. 517–519.
Cohen et al., Med. & Biol. Eng. & Comput., vol. 15, Jul. 1977, pp. 431–437.

Primary Examiner—Kyle L. Howell
Assistant Examiner—John C. Hanley
Attorney, Agent, or Firm—Lowe, King, Price & Becker

[57] ABSTRACT

In a self-training biofeedback system, a physiological signal representing the state of relaxation of a person using the system is applied to a time counter to generate a binary count output representing the relaxation period. A visual indicator connected to the time counter provides the self trained person with a quick display of the measured time period so he can gauge the depth of his relaxation.

20 Claims, 6 Drawing Figures

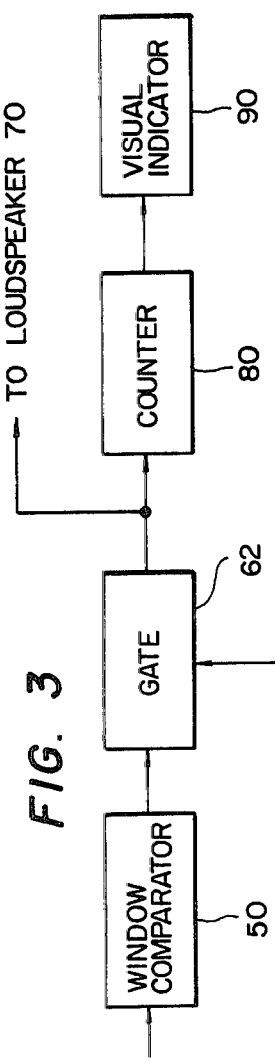
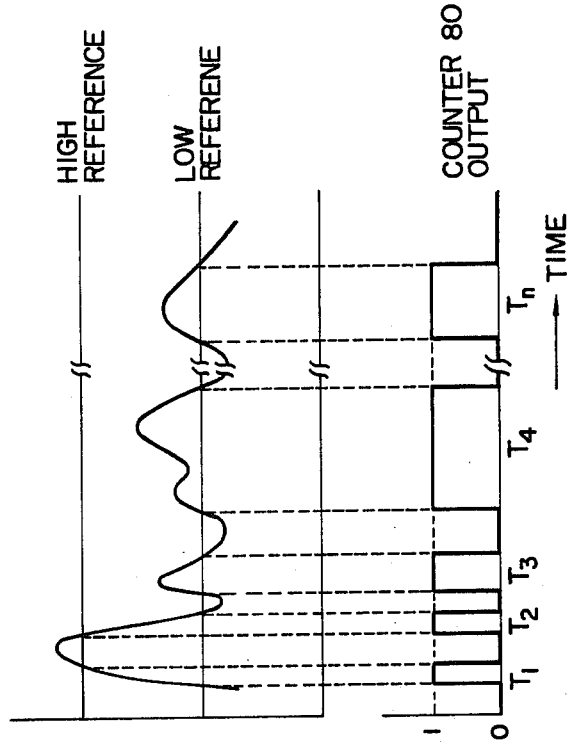
FIG. 3
FIG. 2a
FIG. 2b

METHOD OF AND APPARATUS FOR TESTING AND INDICATING RELAXATION STATE OF A HUMAN SUBJECT

BACKGROUND OF THE INVENTION

The present invention relates to self-training biofeedback systems for indicating the mental condition of a person to assist him in bringing his mind into a state of relaxation.

It is well known that human mental activity can be measured in terms of electrical activity of the brain as represented by the brain waves, or in terms of electrical potential changes measured by electromyographic method, or potential changes at the surface of the skin or temperature at the skin surface. It is also known that these physiological phenomena can be used to control the autonomous nerve system of the person or as a means for rehabilitation of incapacitated people. More specifically, when a human subject is in a relaxed state of mind, the predominant brain waves are the so-called alpha waves and the muscle potential decreases to a low level with an increase in the electrical resistance and temperature of his skin. Conversely, when the subject in a strained or highly excited state, brain waves called beta waves, are predominant and the muscle potential increases with a decrease in skin electrical resistance and temperature.

Thus, an indication of such physiological signals could serve as a guide to lead the person into a relaxed state of mind. This kind of mind control is called "biofeedback" and the apparatus used for such therapy is called a biofeedback system.

Most prior art biofeedback systems, however, are only capable of indicating the presence of a state of relaxation by means of an audible or visual indicator, so that the person using the system remains unaware of the interval while the desired state is maintained. One approach would be to employ a costly recording apparatus comprising stylus which traces the detected signal on a recording sheet, which is unsatisfactory for household use.

SUMMARY OF THE INVENTION

An object of the present invention is to provide an improved self-training biofeedback system for household use which measures the length of time during which the user is in a state of relaxation and gives a visual indication of the measured time on a real time basis.

The state of relaxation is usually attained by the act of meditation. It is usually difficult for laymen to attain a state of complete relaxation. The general tendency is for laymen to repeat the process of going into a state of incomplete relaxation and returning therefrom to an unrelaxed state during the initial stage of meditation. The biofeedback system of the invention provides the user with a quick indication of the persistence of the relaxation state. This allows the user to gauge the depth of relaxation and encourage him to make further attempts to reach the point where his mental and physical stresses are completely liberated.

According to the invention, various modes of time measurement are available. In one embodiment a total count value of relaxation periods is measured and simultaneously indicated. Since the length of sustained relaxation is an indication of the degree of his attainment, each count value of the successively occurring relaxations is indicated by updating the previous count. Thus, in another embodiment the count value is cleared when the person using the system subsequently enters the state of relaxation. In this embodiment, minimum and maximum time counts may also be detected for separate indications to allow the user to compare his attained results. In further embodiments, a ratio of the total time period to a given interval of time during which he has performed meditation is derived.

BRIEF DESCRIPTION OF THE DRAWINGS

The invention is further described by way of example with reference to the accompanying drawings, in which:

FIGS. 2a and 2b are graphic illustrations associated with the embodiment of FIG. 1;

FIG. 3 is an illustration of a modification of the embodiment of FIG. 1;

DETAILED DESCRIPTION

Figure 1:
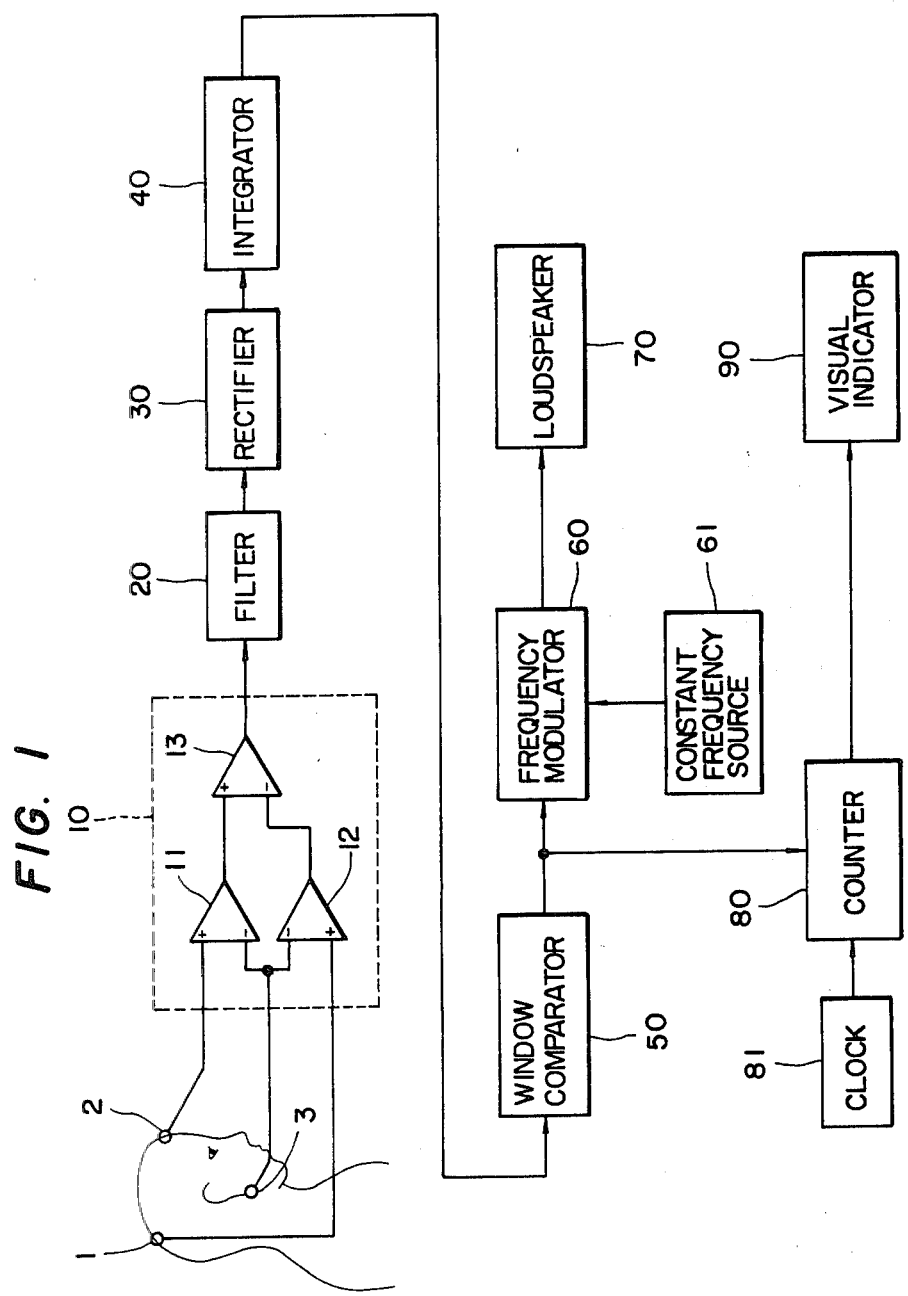
FIG. 1 is an illustration of a first embodiment of the present invention.

Referring now to FIG. 1, electrodes 1 and 2, called the active electrodes, are placed on the scalp of a person using the system near the sources of electrical activity. Electrode 3, called the inactive electrode, is placed on the earlap which is relatively distant from the active electrodes. The active electrodes one and two pick up electrical activities of the brain in the vicinities near them. Signals transduced by electrodes 1 and 2 are supplied to the noninverting inputs of operational amplifiers 11 and 12 which form part of a differential amplifier stage 10 having a total amplification gain of about 1000. The inactive electrode 3 serves as a reference electrode to derive signal supplied to the inverting inputs of the operational amplifiers 11 and 12. The outputs of the amplifiers 11 and 12 are connected to the noninverting and inverting inputs of a third operational amplifier 13, respectively, so that the reference signal from the inactive electrode 3 is cancelled out in the third amplifier 13. The output of the differential amplifier 10 is representative of the difference in amplitude between the signals from the active electrodes 1 and 2. In this way, undesirable noise components which may be present to the active electrodes are effectively reduced to a minimum.

The output signal from the differential amplifier stage 10 is applied to an active filter 20 having an amplification gain of about 100 and a passband frequency in a range from about 7 to 14 Hz to detect alpha brain waves. The signal passing through the filter 20 is applied to a rectifier 30 to generate unipolar pulses which are applied to an integrator 40 having a time constant value of about 1 second. The DC signal from the integrator 40 is applied to a window comparator 50 which detects the presence of alpha brain waves by comparing the input DC signal with low and high reference values (FIG. 2a) which correspond respectively to output levels 1 and 100 microvolts of the active electrodes. Details of the window comparator are described in "Operational Amplifiers, Design and Applications", Tobey, Graeme, Huelsman, McGraw-Hill, pages 364 to 366. Whenever the input DC signal from the integrator 40 falls within this range, the comparator 50 generates a pulse as indicated in FIG. 2b. This pulse is applied on the one hand to a voltage-frequency converter which essentially comprises a frequency modulator 60 and a constant frequency source 61 supplying to the modulator an audio constant frequency signal to the modulator 60. Modulator 60 frequency modulates the constant frequency signal of source 61 at a frequency determined by the output of comparator 50 so that the output of the modulator 60 varies in a range between 50 Hz and 10,000 Hz. The variable frequency output of frequency modulator 60 is applied to a loudspeaker 70 to give an audible indication of the presence of alpha waves. The comparator output is applied on the other hand as an enable input to a counter 80 to enable the counter to respond to clock pulses from a clock source 81 to count the period of each output pulse of the comparator 50. Each count value is accumulated in the counter 80 so that the latter provides a binary representation of a total pulse period of $T_1$, $T_2$ to $T_n$ during which the subject person is under the state of relaxation. A binary visual indicator 90 is connected to the output of the counter 80 to give a visual indication of the count value in decimal numbers.

FIG. 3 is an illustration of a modification of the embodiment of FIG. 1. This embodiment differs from the previous embodiment because: (1) frequency modulator 60 is replaced by a gate 62 which selectively couples the signal from the frequency source 61 to the gate output terminal in response to a logical one output of the comparator 50 and (2) counter 80 is connected to the output of the gate 62 to count the number of oscillations of the frequency source 61 passing through the gate 62. The counted oscillations are accumulated in the counter 80 so that the counter output represents the total period of time during which the comparator 50 output remains in the logical one state.

Figure 4:
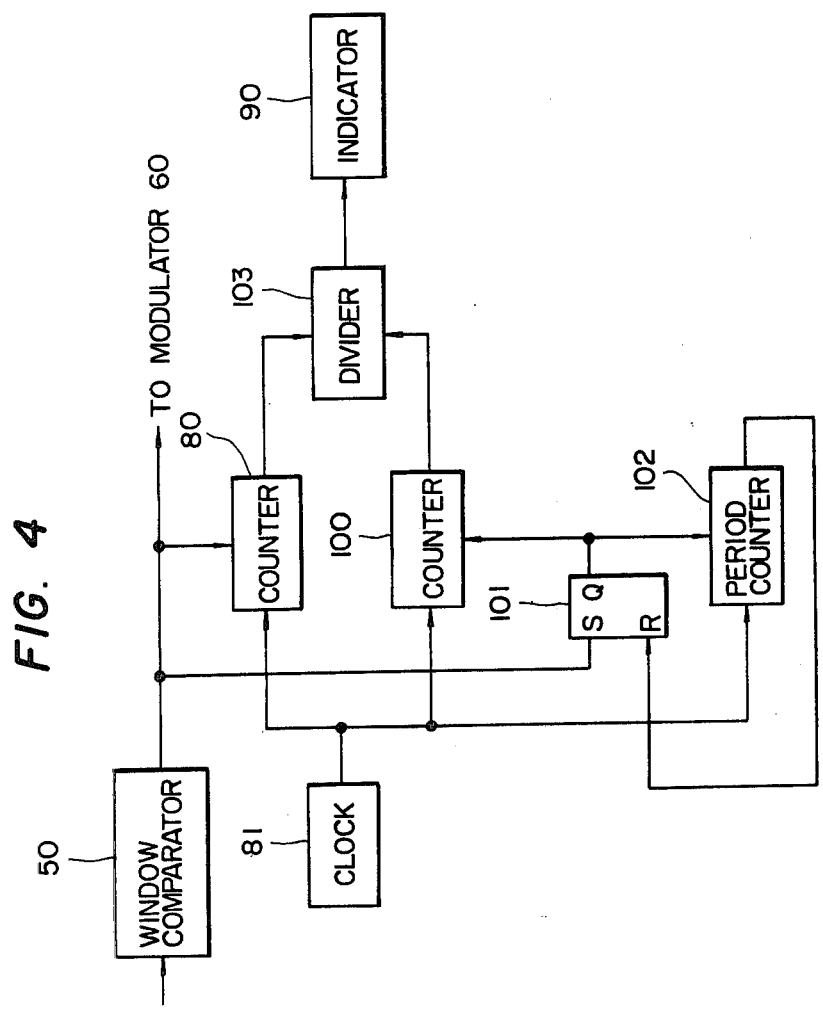
FIG. 4 is an illustration of a second embodiment of the invention.
Figure 5:
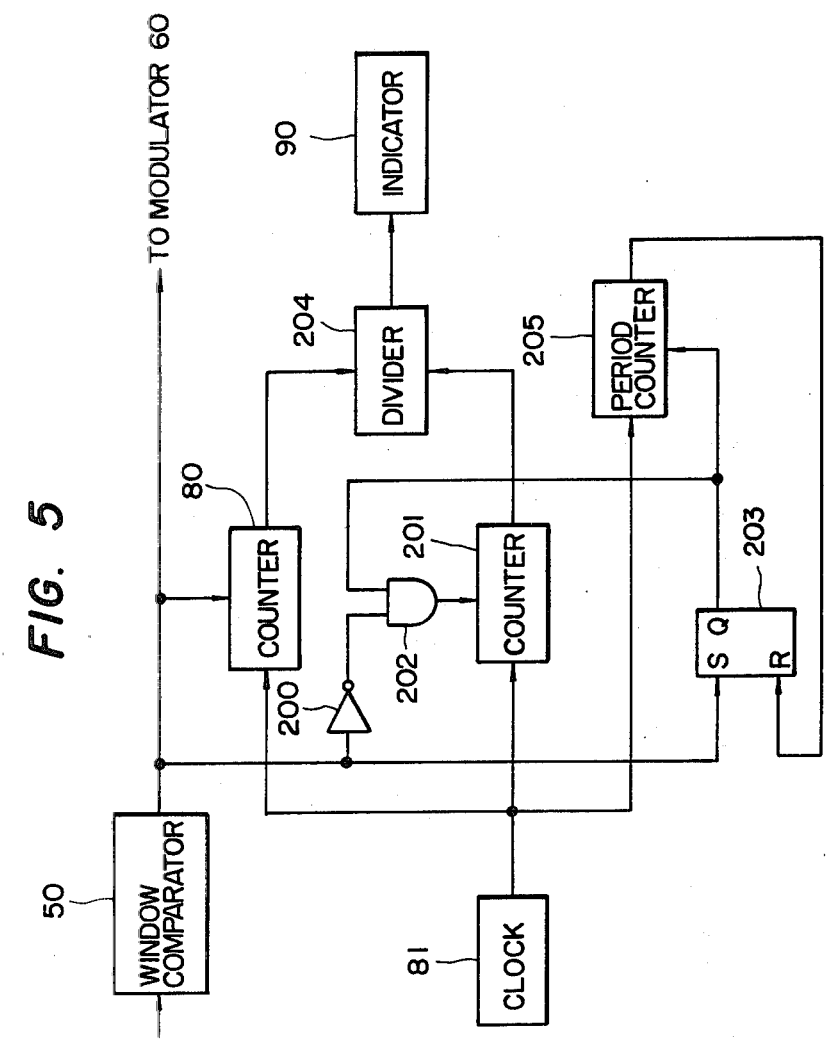
FIG. 5 is an illustration of an alternative embodiment of FIG. 4.

Other embodiments of the invention are shown in FIGS. 4 and 5 wherein parts corresponding to those in FIG. 1 are numbered with corresponding numerals. In FIG. 4, a counter 100 connected to the clock source 81 is enabled in response to flip-flop 101 deriving a logical one output in response to the flip-flop set input responding to a binary one at to the output of the window comparator 50. A period counter 102 receives clock pulses from clock 81 in response to a logical one output from the flip-flop 101. Counter 102 generates an output when a predetermined count value is reached whereupon it resets flip-flop 101. Therefore, the flip-flop 101 remains in the set state for a predetermined period of time. The counter 100 is identical to the counter 80 in that counter 100 provides a binary output representing the counted numbers of clock pulses but counter 100 differs from counter 80 in that the count value in counter 100 is representative of the time interval set by the period counter 102. A digital divider 103 is provided to divide the binary output of counter 80 by the binary output of the counter 100 so that the divider delivers a binary output indicative of the ratio of the total period of the user's relaxation to the predetermined period.

FIG. 5 is an illustration of an alternative embodiment of FIG. 4. In the FIG. 5 embodiment, the ratio of the total period of the user's relaxation to the total period of time in which the user is out of relaxation is derived. To this end, an inverter 200 is connected to the output of the comparator 50 for enabling a counter 201 via an AND gate 202. A flip-flop 203 has a set input connected to the output of the comparator 50 and a Q output connected to an input of the AND gate 202. The AND gate 202 thus provides a logical one to the counter 201 in response to a first occurrence of the user's out-of-relaxation state subsequent to a first occurrence of the state of his relaxation. The counter 201 is repeatedly enabled during the periods in which the user is not in the relaxation state and delivers a binary output indicative of the total count of such intervals to one input of a digital divider 204. This counting operation ceases when the count value in a period counter 205 reaches a predetermined value, resetting the flip-flop 203. The digital divider 204 divides the output of the counter 80 by the output of the counter 201, the resultant division ratio being indicated by the indicator 90.

Figure 6:
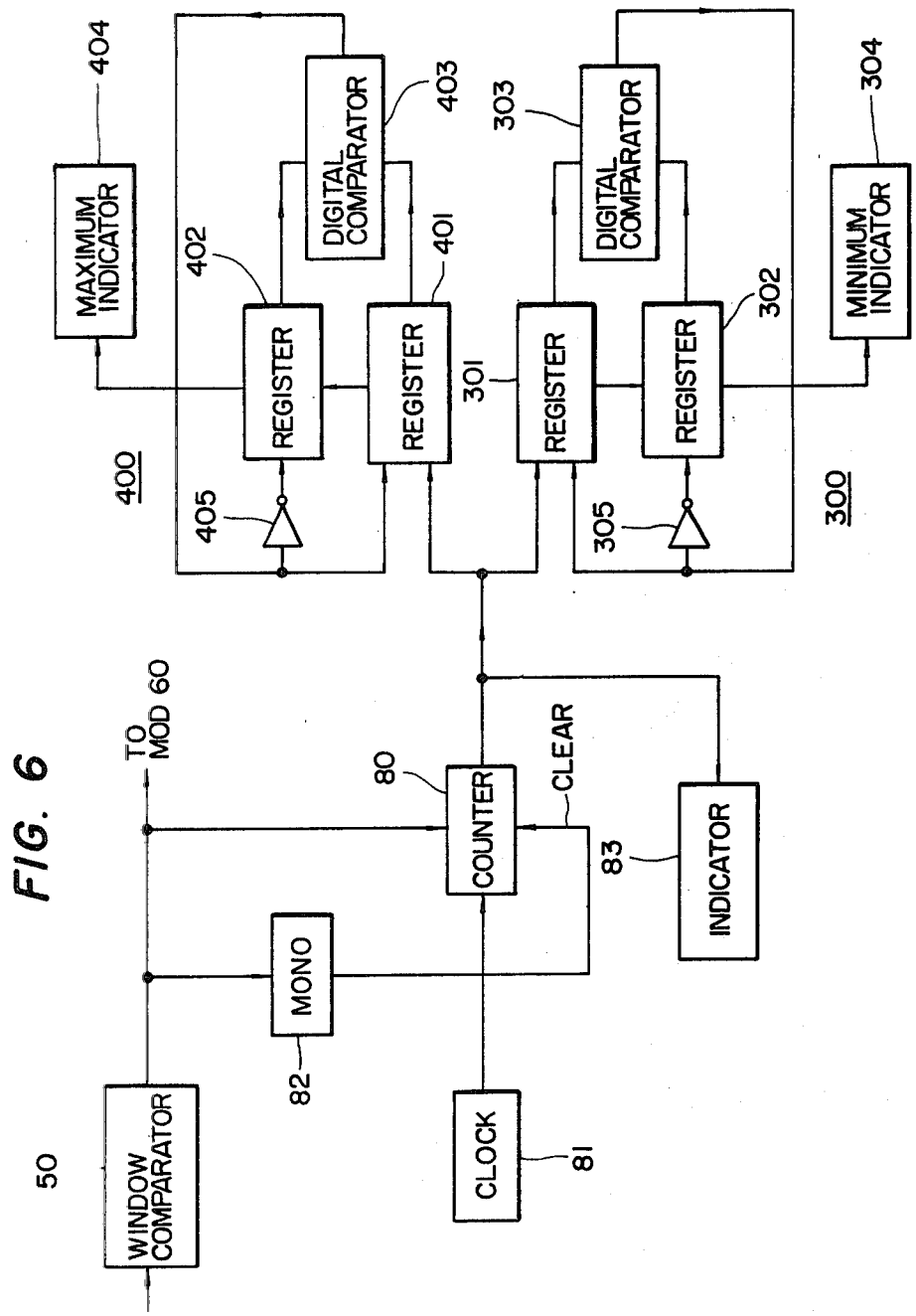
FIG. 6 is an illustration of a third embodiment of the invention.

A further modification of the present invention is shown in FIG. 6 in which the counter 80 is cleared each time the user enters the state of relaxation. This allows the user to gauge the depth of each sustained condition to improve his method of meditation. In this embodiment, the minimum and maximum count values are visually indicated to permit comparison. As illustrated in FIG. 6, the counter 80 is cleared by an output of a monostable multivibrator 82 which is generated each time it detects a leading edge transition of the output of the window comparator 50 to renew the contents of the counter 80 with a subsequent comparator output. The output of the counter 80 is directly indicated by a visual indicator 83. Further included are a minimum detector 300 and a maximum detector 400 which are responsive to the successively updated binary output of the counter 80. The minimum detector 300 comprises a pair of shift registers 301 and 302, a digital comparator 303 having first and second inputs respectively responsive to the outputs of the registers 301 and 302. The register 301 has an input responsive to the output of the counter 80. Register 302 has an input responsive to the output of register 301 and an output supplied to a minimum indicator 304. When the stored contents of the register 302 are smaller in count value than the contents stored in the register 301 the comparator 303 produces a logical one which is coupled to the register 301 to clear the contents. Conversely, when the contents thereof of the register 302 are greater in value than those in register 301, the comparator 303 produces a logical zero which is coupled by inverter 305 to the register 302 as a logical one. The register 302 is cleared in response to the logical one from inverter 305 and the contents of the register 301 are transferred to the register 302, so that the latter is constantly updated with a minimum count value at a given instant of time.

The maximum detector 400 is similar, in certain regards to the minimum detector 300. A register 401 has an input responsive to the output of counter 80. The contents of register 401 are transferred to a shift register 402 when a digital comparator 403 senses that the register 402 has a greater count value than the register 401. More specifically, upon sensing this condition, the comparator 403 provides a logical one signal which is coupled to the register 401 to clear the contents of the register. When the situation is reversed the comparator 403 provides a logical zero which is coupled by inverter 405 as a binary one to the shift register 402 to clear the contents of register 402 and transfer the contents of register 401 to register 402, so that the register 402 is constantly loaded with a maximum count value which is visually indicated by a maximum indicator 404.

What is claimed is:

1. A biofeedback system comprising:
sensing means attached to the scalp of a person for sensing brain waves of a predetermined frequency band and generating therefrom a physiological signal representative of said sensed brain waves;
rectifying means for rectifying said physiological signal for generating a unipolar signal;
integrating means for integrating said unipolar signal;
range detecting means for detecting whether the magnitude of the output of said integrator is in a predetermined range between a first low reference and a second high reference, the output magnitude of the integrating means being susceptible to being lower than the first reference and higher than the second reference;
counter means for accumulatively measuring the duration of the output of said range detecting means and generating therefrom a counter signal representative of the total value of the accumulatively measured durations; and
indicator means for indicating said counter signal.

2. A biofeedback system according to claim 1, further comprising means for continuously measuring the elapse of time and generating therefrom a time lapse signal, and means responsive to said counter signal and said time elapse signal for generating a ratio signal representative of the ratio of said total value of the accumulatively measured durations to said elapse of time and for applying said ratio signal to said indicator means.

3. A biofeedback system according to claim 1, further comprising means for accumulatively measuring the interval between successive outputs of said range detecting means and for generating therefrom an interval signal representative of the total value of said accumulatively measured intervals, and means responsive to said counter signal and said interval signal for generating a ratio signal representative of the ratio of said total value of said accumulatively measured durations of the total value of said accumulatively measured intervals.

4. A biofeedback system as claimed in claim 1, 2 or 3, further comprising a voltage-to-frequency converter connected to the output of said range detecting means and an electroacoustic transducing means connected to said converter for audibly indicating the occurrence of said detected physiological signal.

5. A biofeedback system comprising:
sensing means attached to the scalp of a person for sensing brain waves of a predetermined frequency band and for generating therefrom a physiological signal representative of said sensed brain waves;
rectifying means for rectifying said physiological signal for generating a unipolar signal;
integrating means for integrating said unipolar signal;
range detecting means for detecting whether the magnitude of the output of said integrator is in a predetermined range between a first low reference and a second high reference, the output magnitude of the integrating means being susceptible to being lower than the first reference and higher than the second reference;
counter means for successively measuring the duration of the output of said range detecting means;
a minimum detector coupled to said counter means for detecting a minimum value of said successively measured durations;
a maximum detector coupled to said counter means for detecting a maximum value of said successively measured duration; and
indicator means for indicating said detected minimum and maximum values.

6. Apparatus for testing the relaxation state of a human subject comprising means responsive to brain waves of the subject for deriving a signal having an amplitude indicative of the magnitude of the brain waves in a frequency range corresponding with that of alpha brain waves, and means responsive to the signal for determining the amount of time the signal amplitude is in a range between a first low reference and a second high reference, the signal amplitude being susceptible to being below the first reference and above the second reference.

7. The apparatus of claim 6 wherein the signal deriving means includes active electrodes adapted to be placed on the head of the subject, the first and second references respectively corresponding to levels of approximately 1 and 100 microvolts between the active electrodes.

8. The apparatus of claim 6 further including means responsive to the determining means for indicating the amount of time the signal amplitude is in the range between the first low reference and the second high reference.

9. The apparatus of claim 6 or 8 wherein the signal deriving means includes active electrodes adapted to be placed on the head of the subject for deriving a signal that is a replica of the brain waves, means for bandpass filtering the replica signal over a frequency range corresponding with the alpha brain waves to derive a filtered signal, rectifier means responsive to the filtered signal for deriving a unipolar signal, and means for integrating the unipolar signal to derive the signal indicative of the brain waves.

10. The apparatus of claim 9 wherein the first and second references respectively correspond to levels of approximately 1 and 100 microvolts between the active electrodes.

11. The apparatus of claim 6, 7 or 8 wherein the means for determining includes means responsive to an indication of the total time the subject is tested and an indication of the time the signal amplitude is between the first and second references for deriving an indication of the ratio of time during testing that the signal amplitude is between the first and second references to the total test time.

12. The apparatus of claim 6, 7 or 8 wherein the means for determining includes means responsive to an indication of the total time the subject is tested and an indication of the time the signal amplitude is between the first and second references for deriving an indication of the ratio during testing of the time that the signal amplitude is between the first and second references to the time that the signal amplitude is outside of the first and second references.

13. Apparatus of claim 6, 7 or 8 further including means responsive to a transition from outside the range into the range for restarting the determination of the amount of time the signal amplitude is in the range.

14. A method of testing the relaxation state of a human subject in response to the amplitude of brain waves in a frequency range corresponding with that of alpha brain waves comprising determining and indicating the amount of time the amplitude is in a range between a first low reference and a second high reference, the amplitude being susceptible to being below the first reference and above the second reference.

15. The method of claim 14 wherein the brain waves are detected by active electrodes on the head of the subject, the first and second references respectively corresponding to levels of approximately 1 and 100 microvolts between the active electrodes.

16. The method of claim 14 wherein the amplitude of the brain waves is detected by: active electrodes on the head of the subject receiving a signal that is a replica of the brain waves, filtering the replica signal over a band-pass frequency range corresponding with the alpha brain waves, and integrating the amplitude of the filtered replica.

17. The method of claim 14 wherein the amplitude of the brain waves is detected by: active electrodes on the head of the subject receiving a signal that is a replica of the brain waves, filtering the replica signal over a band-pass frequency range corresponding with the alpha brain waves, and integrating the amplitude of the filtered replica, wherein the first and second references respectively correspond to levels of approximately 1 and 100 microvolts between the active electrodes.

18. The method of claim 14, 15, 16 or 17 wherein the amount of time is determined and indicated as a ratio between the amount of time the amplitude is in the range to the total time the subject is tested.

19. The method of claim 14, 15, 16 or 17 wherein the amount of time is determined and indicated as a ratio between the amount of time the amplitude is in the range to the time the amplitude is out of the range during testing.

20. The method of claim 14, 15, 16 or 17 wherein the determined and indicated time is restarted each time the amplitude enters the range between the first and second references.

* * * * *